(12) United States Patent
Kim et al.

(10) Patent No.: US 10,627,381 B2
(45) Date of Patent: Apr. 21, 2020

(54) METHOD AND APPARATUS FOR CALCULATING SAFETY LEVEL

(71) Applicants: GUMI ELECTRONICS & INFORMATION TECHNOLOGY RESEARCH INSTITUTE, Gyeongsangbuk-do (KR); INDUSTRY ACADEMIC COOPERATION FOUNDATION KEIMYUNG UNIVERSITY, Daegu (KR)

(72) Inventors: Hyung Jin Kim, Gyeongsangbuk-do (KR); Jong Ha Lee, Daegu (KR); Min Ji Choi, Gyeongsangbuk-do (KR)

(73) Assignees: GUMI ELECTRONICS & INFORMATION TECHNOLGY RESEARCH INSTITUTE, Gyeongsangbuk-do (KR); INDUSTRY ACADEMIC COOPERATION FOUNDATION KEIMYUNG UNIVERSITY, Daegu (KR)

( * ) Notice: Subject to any disclaimer, the term of this patent is extended or adjusted under 35 U.S.C. 154(b) by 0 days.

(21) Appl. No.: 16/316,923

(22) PCT Filed: Dec. 12, 2017

(86) PCT No.: PCT/KR2017/014534
§ 371 (c)(1),
(2) Date: Jan. 10, 2019

(87) PCT Pub. No.: WO2018/212423
PCT Pub. Date: Nov. 22, 2018

(65) Prior Publication Data
US 2019/0250136 A1 Aug. 15, 2019

(30) Foreign Application Priority Data
May 16, 2017 (KR) .................. 10-2017-0060513

(51) Int. Cl.
*G08B 21/14* (2006.01)
*G01N 33/00* (2006.01)
(Continued)

(52) U.S. Cl.
CPC ....... *G01N 33/0065* (2013.01); *A61B 5/0402* (2013.01); *A61B 5/04012* (2013.01);
(Continued)

(58) Field of Classification Search
None
See application file for complete search history.

(56) References Cited

U.S. PATENT DOCUMENTS

2004/0017300 A1* 1/2004 Kotzin ............... G08B 21/0453
340/870.11
2017/0069193 A1* 3/2017 Schmidt ................. G08B 21/14

FOREIGN PATENT DOCUMENTS

JP 2002287846 A 10/2002
JP 2014100473 A 6/2014
(Continued)

OTHER PUBLICATIONS

PCT Search Report dated Mar. 21, 2018 for PCT Application No. PCT/KR2017/014354.
(Continued)

*Primary Examiner* — John F Mortell
(74) *Attorney, Agent, or Firm* — EIP US LLP (57) ABSTRACT

Provided is a method and apparatus for calculating a safety grade of a working environment that may receive harmful gas information from a gas sensor configured to detect a harmful gas to calculate a safety grade, receive biometric information of a user from a biometric sensor configured to measure the biometric information of the user, calculate a
(Continued)

safety grade for the user based on the harmful gas information and the biometric information, and output the calculated safety grade.

14 Claims, 6 Drawing Sheets

(51) Int. Cl.
| | |
|---|---|
| *G06N 20/00* | (2019.01) |
| *G08B 21/18* | (2006.01) |
| *A61B 5/117* | (2016.01) |
| *A61B 5/0402* | (2006.01) |
| *A61B 5/0488* | (2006.01) |
| *A61B 5/00* | (2006.01) |
| *A61B 5/0476* | (2006.01) |
| *G06N 3/02* | (2006.01) |
| *A61B 5/04* | (2006.01) |
| *G06Q 10/06* | (2012.01) |
| *G06Q 50/26* | (2012.01) |

(52) U.S. Cl.
CPC .......... *A61B 5/0476* (2013.01); *A61B 5/0488* (2013.01); *A61B 5/117* (2013.01); *A61B 5/7267* (2013.01); *A61B 5/746* (2013.01); *G01N 33/0036* (2013.01); *G06N 3/02* (2013.01); *G06N 20/00* (2019.01); *G06Q 10/0635* (2013.01); *G06Q 50/265* (2013.01); *G08B 21/14* (2013.01); *G08B 21/182* (2013.01); *A61B 2503/20* (2013.01); *A61B 2560/0252* (2013.01); *A61B 2562/029* (2013.01); *G01N 33/004* (2013.01)

(56) References Cited

FOREIGN PATENT DOCUMENTS

| | | | |
|---|---|---|---|
| KR | 1020110053107 | A | 5/2011 |
| KR | 1020110077295 | A | 7/2011 |
| KR | 1020130075328 | A | 7/2013 |
| KR | 1020150121970 | A | 8/2015 |
| KR | 101663572 | B1 | 3/2016 |
| KR | 1020160038600 | A | 3/2016 |
| KR | 1020160075040 | A | 1/2017 |

OTHER PUBLICATIONS

PCT Written Opinion dated Mar. 21, 2018 for PCT Application No. PCT/KR2017/014354.

* cited by examiner

METHOD AND APPARATUS FOR CALCULATING SAFETY LEVEL

TECHNICAL FIELD

Embodiments relate to technology for calculating a safety grade of a workplace, and more particularly, to a method and apparatus for calculating a safety grade using a gas sensor.

BACKGROUND ART

A harmful gas may be produced in a special space such as a scene of fire or a confined underground workspace. A worker may recognize a colored and odorous gas, but not a colorless and odorless gas. When the worker is exposed to an environment with a harmful gas for a predetermined time, an emergency may occur. For example, in a case in which a worker works in an underground environment where a concentration of carbon monoxide is greater than or equal to a predetermined level, it may harm a heath of the worker. If it is possible to detect a harmful gas and determine a degree of danger using a device carried by the worker, the worker may be protected from a harmful environment.

Korean Patent Publication No. 10-1663572 (published on Sep. 30, 2016) discloses a monitoring system of working environment for ensuring safety of workers. The publication discloses an environment monitoring module including a sensor unit that includes an oxygen sensor to detect a preset gas and measure a concentration of oxygen in the air when power is supplied thereto, a control unit to control an operation of the sensor unit, and a communication unit electrically connected to the control unit and connected to a smart phone of a worker through wired and wireless communication, and an application installed on the smart phone to determine a dangerous situation by receiving a detection value of the sensor unit through the communication unit and perform a warning signal in response to the determination of the dangerous situation.

DISCLOSURE OF INVENTION

Technical Goals

An aspect provides a method and apparatus for calculating a safety grade.

An aspect provides a method and apparatus for calculating a safety grade based on harmful gas information and biometric information.

Technical Solutions

According to an aspect, there is provided a method of calculating a safety grade, the method receiving harmful gas information from a gas sensor configured to detect a harmful gas, receiving biometric information of a user from a biometric sensor configured to measure the biometric information of the user, calculating a safety grade for the user based on the harmful gas information and the biometric information, and outputting the calculated safety grade.

The calculating may include identifying the user, obtaining information related to the identified user, and calculating the safety grade for the user based on the information related to the user and the biometric information.

The calculating may further include determining a type of the harmful gas based on the harmful gas information, and the obtaining may include obtaining the information related to the user with respect to the type of the harmful gas.

The information related to the user may be information related to a standard electrocardiogram (ECG) of the user, and the biometric information may be information related to a target ECG when exposed to the harmful gas.

The calculating of the safety grade for the user based on the information related to the user and the biometric information may include extracting a feature of the standard ECG and a feature of the target ECG, and calculating the safety grade based on the feature of the standard ECG and the feature of the target ECG.

The information related to the user may be information related to a standard electroencephalogram (EEG) of the user, and the biometric information may be information related to a target EEG when exposed to the harmful gas.

The information related to the user may be information related to a standard electromyogram (EMG) of the user, and the biometric information may be information related to a target EMG when exposed to the harmful gas.

The information related to the user may be information related to a standard ECG, a standard EEG and a standard EMG of the user, and the biometric information may be information related to a target ECG, a target EEG and a target EMG when exposed to the harmful gas.

The calculating of the safety grade for the user based on the information related to the user and the biometric information may include extracting a feature of the standard ECG and a feature of the target ECG, calculating a first safety grade based on the feature of the standard ECG and the feature of the target ECG, extracting the feature of the standard ECG and a feature of the target EEG, calculating a second safety grade based on the feature of the standard ECG and the feature of the target EEG, extracting the feature of the standard ECG and a feature of the target EMG, calculating a third safety grade based on the feature of the standard ECG and the feature of the target EMG, and calculating a final safety grade based on the first safety grade, the second safety grade and the third safety grade.

The calculating may include calculating the safety grade for the user using a machine learning algorithm.

The machine learning algorithm may be pre-trained to calculate a safety grade based on a biometric characteristic of the user and a concentration of the harmful gas.

The machine learning algorithm may be pre-trained to further consider air temperature and humidity factors.

The method may further include transmitting an alarm to an external device in a case in which the calculated safety grade is less than a preset threshold.

The alarm may include a position of the user and the harmful gas information.

According to another aspect, there is provided an apparatus for calculating a safety grade, the apparatus including a memory configured to store a program for calculating a safety grade, and a processor configured to execute the program, wherein the program may be configured to perform receiving harmful gas information from a gas sensor configured to detect a harmful gas, receiving biometric information of a user from a biometric sensor configured to measure the biometric information of the user, calculating a safety grade for the user based on the harmful gas information and the biometric information, and outputting the calculated safety grade.

Effects

It is possible to provide a method and apparatus for calculating a safety grade of a working environment.

It is possible to provide a method and apparatus for calculating a safety grade based on harmful gas information and biometric information.

BEST MODE FOR CARRYING OUT THE INVENTION

Hereinafter, embodiments will be described in detail with reference to the accompanying drawings. However, the scope of the present application is not limited to the embodiments. In the drawings, like reference numerals are used for like elements.

Various alterations and modifications may be made to the examples. Here, the examples are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which examples belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the embodiments with reference to the accompanying drawings, like reference numerals refer to like constituent elements and a repeated description related thereto will be omitted. When it is determined detailed description related to a related known function or configuration they may make the purpose of the embodiments unnecessarily ambiguous in describing the embodiments, the detailed description will be omitted here.

Figure 1:
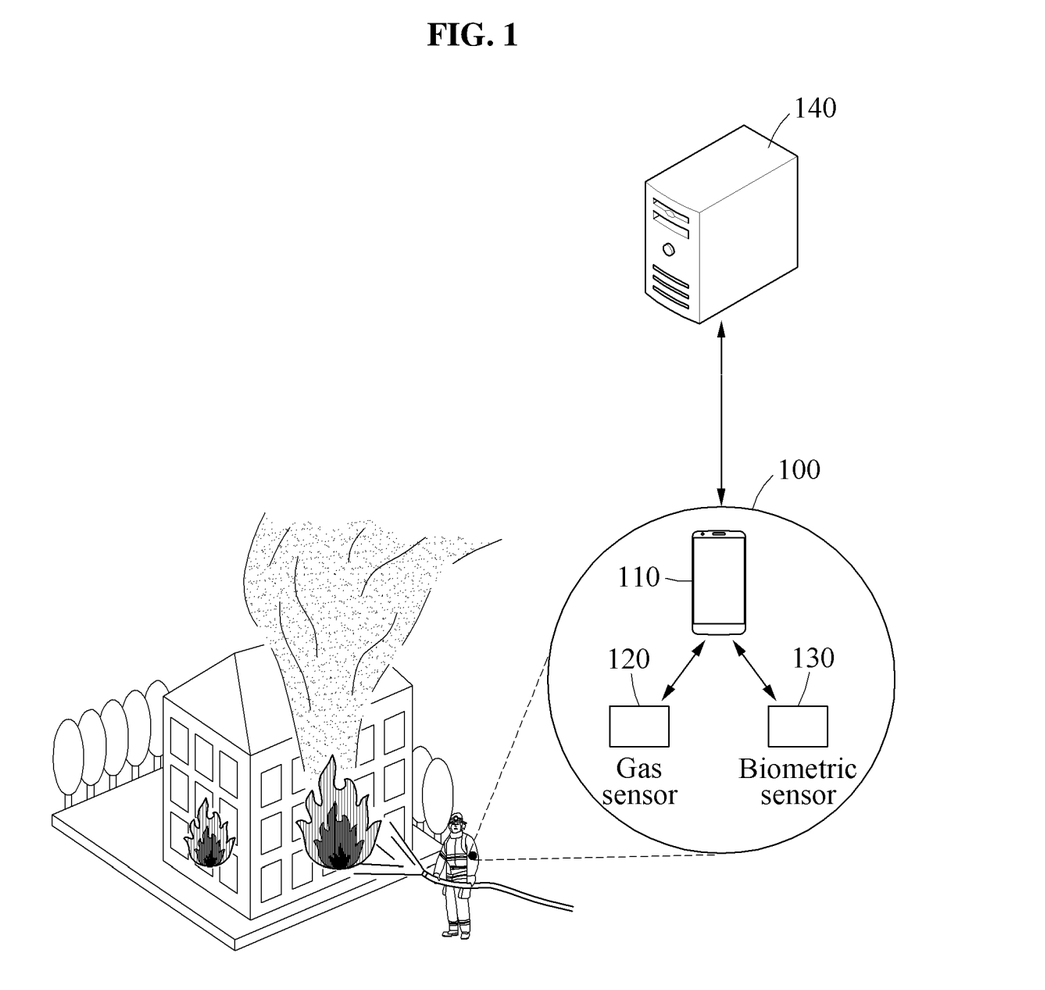
FIG. 1 illustrates a safety management system according to an embodiment.

FIG. 1 illustrates a safety management system according to an embodiment.

The safety management system may include a safety grade calculating system 100 and a management server 140.

The safety grade calculating system 100 may include a safety grade calculating apparatus 110, a gas sensor 120 and a biometric sensor 130. The gas sensor 120 may be attached to an outfit (for example, a working cap or a working garment) of a user. The biometric sensor 130 may measure a biometric signal of the user, and be attached to be in contact with the skin of the user to measure the biometric signal. The safety grade calculating apparatus 110 may be a portable device, and carried by the user. The safety grade calculating apparatus 110 may transmit and receive information or data to and from the gas sensor 120 and the biometric sensor 130 using wireless communication.

The safety grade calculating apparatus 110 may calculate a safety grade of an environment where the user is positioned based on the information received from the gas sensor 120 and the biometric sensor 130. The user may determine whether to work in the corresponding environment based on the safety grade.

The management server 140 may manage the safety grade calculating system 100. For example, the management server 140 may receive the calculated safety grade from the safety grade calculating apparatus 110, and take an action corresponding to the safety grade. For example, the management server 140 may transmit a rescue request to a fire station. The management server 140 may establish a database and transmit necessary information to the safety grade calculating apparatus 110.

Hereinafter, a method of calculating a safety grade will be described in detail with reference to FIGS. 2 through 6.

Figure 2:
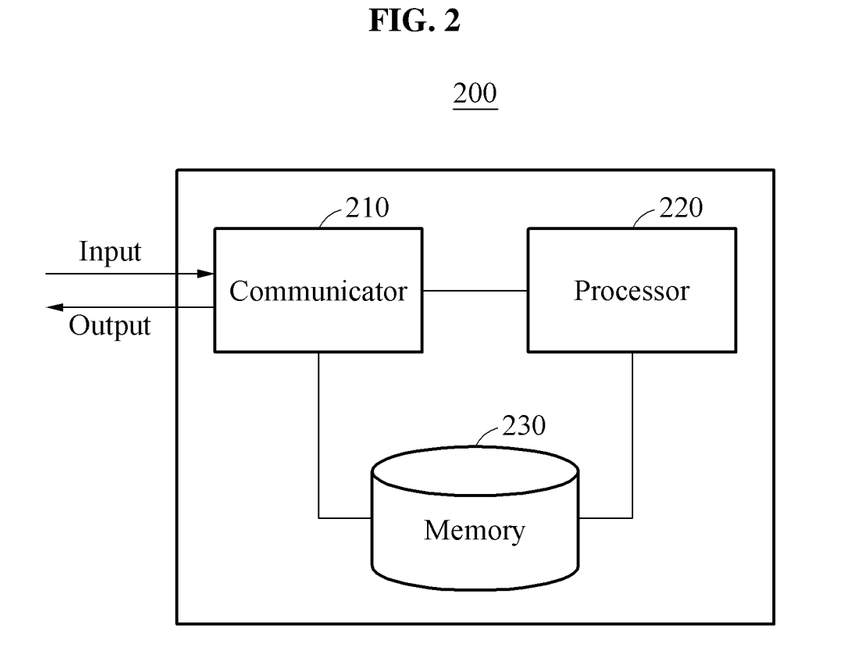
FIG. 2 illustrates a configuration of a safety grade calculating apparatus according to an embodiment.

FIG. 2 illustrates a configuration of a safety grade calculating apparatus according to an embodiment.

A safety grade calculating apparatus 200 may include a communicator 210, a processor 220 and a memory 230. The safety grade calculating apparatus 200 may correspond to the safety grade calculating apparatus 110 of FIG. 1. For example, the safety grade calculating apparatus 200 may be an apparatus for independently calculating a safety grade. In another example, the safety grade calculating apparatus 200 may be an apparatus capable of executing an application, like a smart-phone.

The communicator 210 may be connected to the processor 220 and the memory 230 and transmit and receive data thereto and therefrom. The communicator 210 may be connected to another external device and transmit and receive data thereto and therefrom. Hereinafter, transmitting and receiving "A" may refer to transmitting and receiving information or data representing "A".

The communicator 210 may be implemented as a circuitry in the safety grade calculating apparatus 200. For example, the communicator 210 may include an internal bus and an external bus. In another example, the communicator 210 may be an element configured to connect the safety grade calculating apparatus 200 and the external device. The communicator 210 may be an interface. The communicator 210 may receive data from the external device and transmit the data to the processor 220 and the memory 230.

The processor 220 may process the data received by the communicator 210 and data stored in the memory 230. The "processor" may be a hardware-implemented data processing device having a circuit with a physical structure to perform desired operations. For example, the desired operations may include codes or instructions included in a program. The hardware-implemented data processing device may include a microprocessor, a central processing unit (CPU), a processor core, a multi-core processor, a multiprocessor, an application-specific integrated circuit (ASIC), and a field programmable gate array (FPGA).

The processor 220 may execute computer-readable codes (for example, software) stored in a memory (for example, the memory 230) and instructions triggered by the processor 230.

The memory 230 may store the data received by the communicator 210 and the data processed by the processor 220. For example, the memory 230 may store the program. The stored program may be a set of syntaxes coded and executable by the processor 220 to calculate a safety grade.

In an aspect, the memory 230 may include at least one volatile memory, non-volatile memory, random access memory (RAM), flash memory, hard disk drive and optical disk drive.

The memory 230 may store a command set (for example, software) to operate the safety grade calculating apparatus 200. The command set to operate the safety grade calculating apparatus 200 may be executed by the processor 220.

The communicator 210, the processor 220 and the memory 230 will be described further with reference to FIGS. 3 through 6.

Figure 3:
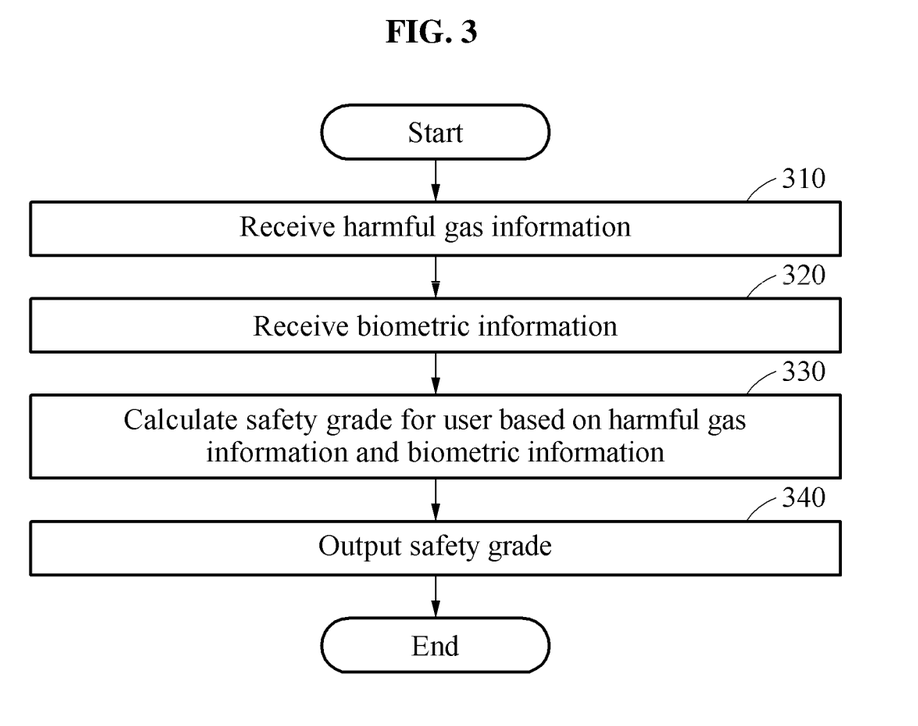
FIG. 3 is a flowchart illustrating a safety grade calculating method according to an embodiment.

FIG. 3 is a flowchart illustrating a safety grade calculating method according to an embodiment.

The following operations 310 through 340 may be performed by the safety grade calculating apparatus 200 of FIG. 2.

In operation 310, the communicator 210 may receive harmful gas information from a gas sensor configured to detect a harmful gas. The harmful gas information may include a type and a concentration of the gas.

The gas sensor may be the gas sensor 120 of FIG. 1. The gas sensor may be manufactured as a system on chip (SoC), but is not limited thereto. The gas sensor may identify various types of harmful gases, and measure concentrations of the harmful gases. The gas sensor may be attached to an outfit of a user to effectively measure a harmful gas in a working environment. The harmful gas information may refer to information related to a gas determined to be the harmful gas. The gas sensor may transmit the harmful gas information to the safety grade calculating apparatus 200 using an embedded communication device.

In operation 320, the communicator 210 may receive biometric information of the user from a biometric sensor configured to measure the biometric information of the user.

The biometric sensor may be the biometric sensor 130 of FIG. 1. The biometric sensor may be manufactured as an SoC, but is not limited thereto. The biometric sensor may be attached directly to the skin of the user. For example, the biometric sensor may be a patch type.

There may be various types of biometric sensors, and an electrocardiogram (ECG), an electroencephalogram (EEG), an electromyogram (EMG), a breath, and a blood oxygen saturation may be measured depending on the types of the sensors. The biometric information may be information measured through the biometric sensor. The biometric sensor may transmit the biometric information to the safety grade calculating apparatus 200 using an embedded communication device.

In operation 330, the processor 220 may calculate a safety grade for the user based on the harmful gas information and the biometric information. For example, the safety grade may be calculated numerically. A relatively high safety grade may indicate a relatively high safety.

In an aspect, the processor 220 may calculate the safety grade for the user using a machine learning algorithm. The machine learning algorithm may be an algorithm pre-trained to calculate a safety grade based on a biometric characteristic of a user and a concentration of a harmful gas. The machine learning algorithm may be pre-trained to further consider air temperature and humidity factors.

The example of calculating the safety grade will be described further with reference to FIGS. 4 and 5.

In operation 340, the processor 220 may output the calculated safety grade.

For example, the processor 220 may control a display of the safety grade calculating apparatus 200 to output the safety grade. The processor 220 may adjust a brightness of the display to its maximum and output the safety grade such that the user may easily recognize the output safety grade. In another example, the processor 220 may output a vibration corresponding to the calculated safety grade through a vibrator of the safety grade calculating apparatus 200. A vibration pattern may be mapped in advance to each level of the safety grade. With respect to a relatively low safety grade, a relatively strong vibration with a relatively frequent vibration pattern may be output.

In a case in which the user is wearing a wearable device including a display, and the safety grade calculating apparatus 200 is connected to the wearable device, the processor 220 may output the calculated safety grade through the display of the wearable device. For example, the wearable device may be an eyewear type or a helmet type.

In an aspect, in a case in which the calculated safety grade is less than a preset threshold, and a floor plan or an architectural plan of a workplace is stored in the safety grade calculating apparatus 200, an escape route may be output using the floor plan or the architectural plan. In a case in which the safety grade calculating apparatus 200 is capable of acquiring a position of the safety grade calculating apparatus 200 using the global positioning system (GPS), the processor 220 may provide the escape route by displaying a current position on the floor plan or the architecture plan.

Figure 4:
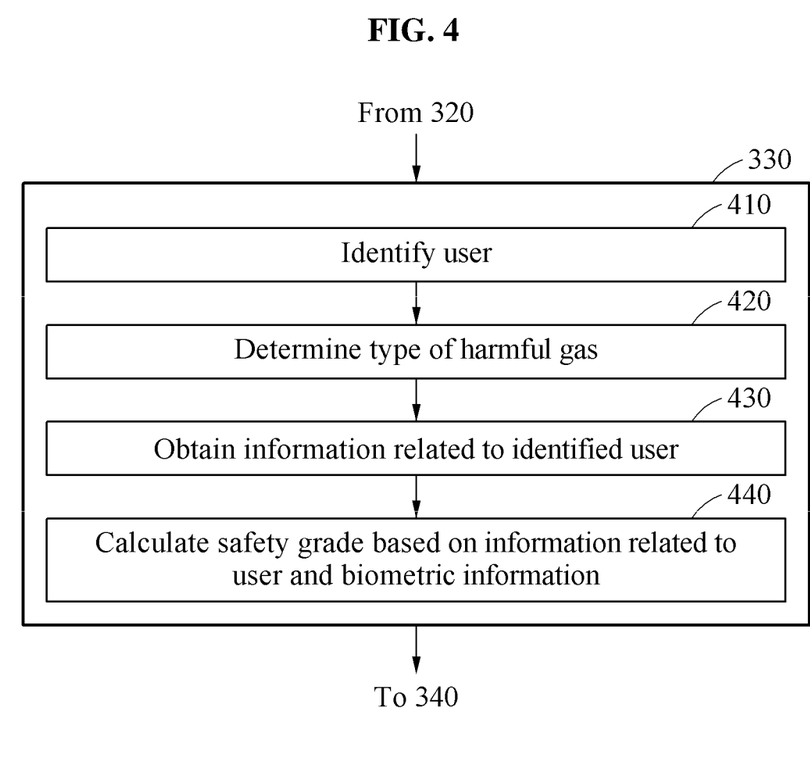
FIG. 4 is a flowchart illustrating an example of calculating a safety grade for an identified user according to an embodiment.

FIG. 4 is a flowchart illustrating an example of calculating a safety grade for an identified user according to an embodiment.

Operation 330 of FIG. 3 may include the following operations 410 through 440. The following operations 410 and 440 may be performed by the machine learning algorithm described with reference to FIG. 3. The machine learning algorithm may be performed by the processor 220.

In operation 410, the processor 220 may identify the user of the safety grade calculating apparatus 200. For example, when the user inputs information to identify the user into the safety grade calculating apparatus 200, the user may be identified. In another example, the user may be identified based on the biometric information received from the biometric sensor. In a case in which the biometric information received from the biometric sensor corresponds to a pre-stored biometric pattern, the user may be identified.

In operation 420, the processor 220 may determine a type of the harmful gas based on the harmful gas information. For example, the harmful gas information may include the type of the harmful gas.

In operation 430, the processor 220 may obtain information related to the identified user. For example, information related to the user with respect to the type of the harmful gas may be obtained. The information related to the user may be information associated with at least one of a standard ECG, a standard EEG, and a standard EMG of the user. The standard ECG, the standard EEG, and the standard EMG of the user may be measured in advance for each type of the harmful gas, and corresponding results may be stored.

In operation 440, the processor 220 may calculate the safety grade based on the information related to the user and the biometric information. The biometric information may be information related to at least one of an ECG, a standard EEG, and a standard EMG of the user when exposed to the harmful gas. The ECG of the user when exposed to the harmful gas will be referred to as a target ECG, the EEG of the user when exposed to the harmful gas will be referred to as a target EEG, and the EMG of the user when exposed to the harmful gas will be referred to as a target EMG. For example, the processor 220 may calculate the safety grade based on at least one of the target ECG, the target EEG and the target EMG. For example, the safety grade may be calculated based on a similarity between the standard ECG and the target ECG.

The example of calculating the safety grade based on at least one of the target ECG, the target EEG and the target EMG will be described further below with reference to FIG. 5.

Figure 5:
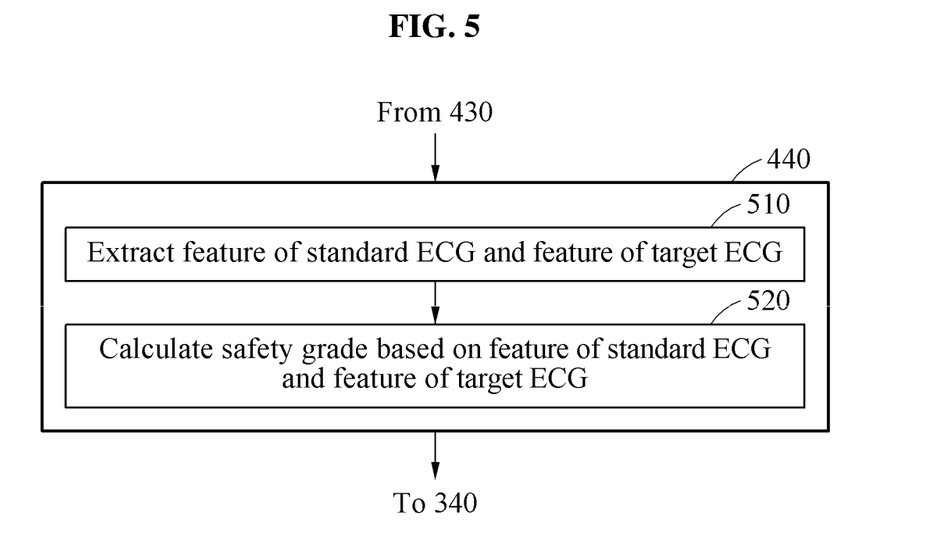
FIG. 5 is a flowchart illustrating an example of calculating a safety grade based on a standard electrocardiogram (ECG) and a target ECG according to an embodiment.

FIG. 5 is a flowchart illustrating an example of calculating a safety grade based on a standard ECG and a target ECG according to an embodiment.

Operation 440 of FIG. 4 may include the following operations 510 and 520.

In operation 510, the processor 220 may extract a feature of the standard ECG and a feature of the target ECG. Features of an ECG may include frequency of heart beat, a maximum amplitude of a signal, a P-wave, a QRS-wave, a T-wave, a U-wave, and a T-wave.

In operation 520, the processor 220 may calculate the safety grade based on the feature of the standard ECG and the feature of the target ECG. For example, the processor 220 may calculate the safety grade based on a similarity between the features. In another example, the processor 220 may calculate the safety grade further based on the harmful gas information. As a concentration of the harmful gas is relatively high, a weight to decrease the safety grade may be assigned. As a toxicity of the harmful gas is relatively high, a weight to decrease the safety grade may be assigned.

Operations 510 and 520 are related to the example of calculating the safety grade based on the feature of the standard ECG and the feature of the target ECG, but may also be applicable to an example of calculating the safety grade based on a feature of the standard EEG and a feature of the target EEG and an example of calculating the safety grade based on a feature of the standard EMG and a feature of the target EMG.

In an aspect, after operation 520 is performed, a final safety grade may be calculated based on a first safety grade calculated using the target ECG, a second safety grade calculated using the target EEG, and a third safety grade calculated using the target EMG. For example, an average of the first safety grade, the second safety grade and the third safety grade may be calculated as the final safety grade.

Figure 6:
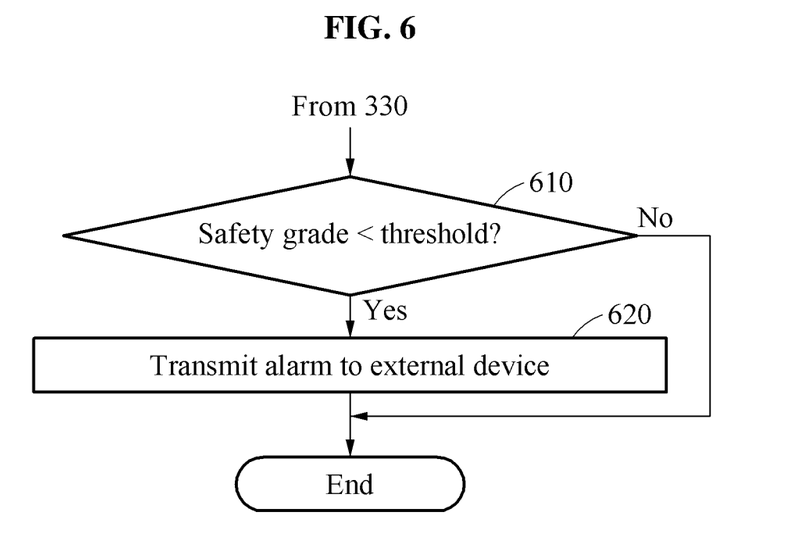
FIG. 6 is a flowchart illustrating an example of transmitting an alarm to an external device according to an embodiment.

FIG. 6 is a flowchart illustrating an example of transmitting an alarm to an external device according to an embodiment.

After operation 330 of FIG. 3 is performed, the following operations 610 and 620 may be performed additionally.

In operation 610, the processor 220 may determine whether the calculated safety grade is less than a preset threshold. The threshold may be set differently based on at least one of the type of the harmful gas and a characteristic of the user.

In operation 620, in a case in which the calculated safety grade is less than the threshold, the processor 220 may transmit an alarm to an external device through the communicator 210. The alarm may include a position of the user and the harmful gas information. For example, the external device may be the management server 140 of FIG. 1. In another example, the external device may be a server of a fire station. In still another example, the external device may be a safety grade calculating apparatus used by another nearby user.

Software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The method according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

The invention claimed is:

1. A method of calculating a safety grade, the method comprising:
receiving harmful gas information from a gas sensor configured to detect a harmful gas;
receiving biometric information of a user from a biometric sensor configured to measure the biometric information of the user;
calculating a safety grade for the user based on the harmful gas information and the biometric information; and
outputting the calculated safety grade, wherein the calculating comprises:
   identifying the user;
   obtaining information related to the identified user; and
   calculating the safety grade for the user based on the information related to the user and the biometric information,
wherein the information related to the user is information related to a standard electromyogram (EMG) of the user, and
the biometric information is information related to a target EMG when exposed to the harmful gas.

2. The method of claim 1, wherein the calculating further comprises determining a type of the harmful gas based on the harmful gas information, and
   the obtaining comprises obtaining the information related to the user with respect to the type of the harmful gas.

3. The method of claim 1, wherein the information related to the user is information related to a standard electrocardiogram (ECG) of the user, and
   the biometric information is information related to a target ECG when exposed to the harmful gas.

4. The method of claim 3, wherein the calculating of the safety grade for the user based on the information related to the user and the biometric information comprises:
   extracting a feature of the standard ECG and a feature of the target ECG; and
   calculating the safety grade based on the feature of the standard ECG and the feature of the target ECG.

5. The method of claim 1, wherein the information related to the user is information related to a standard electroencephalogram (EEG) of the user, and
   the biometric information is information related to a target EEG when exposed to the harmful gas.

6. The method of claim 1, wherein the information related to the user is information related to a standard ECG, a standard EEG and the standard EMG of the user, and
   the biometric information is information related to a target ECG, a target EEG and the target EMG when exposed to the harmful gas.

7. The method of claim 6, wherein the calculating of the safety grade for the user based on the information related to the user and the biometric information comprises:
   extracting a feature of the standard ECG and a feature of the target ECG;
   calculating a first safety grade based on the feature of the standard ECG and the feature of the target ECG;
   extracting the feature of the standard EEG and a feature of the target EEG;
   calculating a second safety grade based on the feature of the standard EEG and the feature of the target EEG;
   extracting the feature of the standard EMG and a feature of the target EMG;
   calculating a third safety grade based on the feature of the standard EMG and the feature of the target EMG; and
   calculating a final safety grade based on the first safety grade, the second safety grade and the third safety grade.

8. The method of claim 1, wherein the calculating comprises calculating the safety grade for the user using a machine learning algorithm.

9. The method of claim 8, wherein the machine learning algorithm is pre-trained to calculate a safety grade based on a biometric characteristic of the user and a concentration of the harmful gas.

10. The method of claim 9, wherein the machine learning algorithm is pre-trained to further consider air temperature and humidity factors.

11. The method of claim 1, further comprising:
   transmitting an alarm to an external device in a case in which the calculated safety grade is less than a preset threshold.

12. The method of claim 11, wherein the alarm includes a position of the user and the harmful gas information.

13. A non-transitory computer-readable medium comprising a program for instructing a computer to perform the method of claim 1.

14. An apparatus for calculating a safety grade, the apparatus comprising:
   a memory configured to store a program for calculating a safety grade; and
   a processor configured to execute the program,
   wherein the program is configured to perform:
   receiving harmful gas information from a gas sensor configured to detect a harmful gas;
   receiving biometric information of a user from a biometric sensor configured to measure the biometric information of the user;
   calculating a safety grade for the user based on the harmful gas information and the biometric information; and
   outputting the calculated safety grade,
      wherein the calculating comprises:
         identifying the user;
         obtaining information related to the identified user; and
         calculating the safety grade for the user based on the information related to the user and the biometric information,
      wherein the information related to the user is information related to a standard electromyogram (EMG) of the user, and
the biometric information is information related to a target EMG when exposed to the harmful gas.

* * * * *